United States Patent [19]

Goldberg

[11] Patent Number: 5,005,972
[45] Date of Patent: Apr. 9, 1991

[54] REFRACTOMETER READOUT SYSTEM

[76] Inventor: Herbert F. Goldberg, 195 Heath's Bridge Rd., Concord, Mass. 01742

[21] Appl. No.: 469,343

[22] Filed: Jan. 24, 1990

[51] Int. Cl.$^5$ .............................................. G01N 21/41
[52] U.S. Cl. ...................................... 356/135; 356/128
[58] Field of Search ................................ 356/128–137, 356/139; 350/253

[56] References Cited

U.S. PATENT DOCUMENTS

| | | | |
|---|---|---|---|
| 253,639 | 6/1926 | Wilson | 356/139 |
| 2,633,053 | 3/1953 | Hansen | 356/135 |
| 2,729,137 | 1/1956 | Forrest | 356/137 |
| 3,279,309 | 10/1966 | Goldberg | 350/253 |

Primary Examiner—F. L. Evans
Assistant Examiner—K. P. Hantis

[57] ABSTRACT

A scale for use in critical angle hand refractometers of conventional design permitting direct numerical readout of every scale division.

7 Claims, 3 Drawing Sheets

DEGREES BRIX

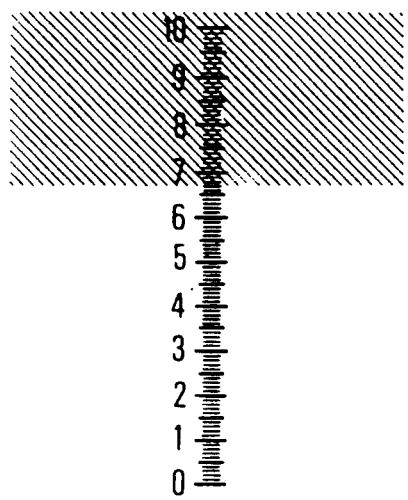
DEGREES BRIX
FIG. 2A (PRIOR ART)
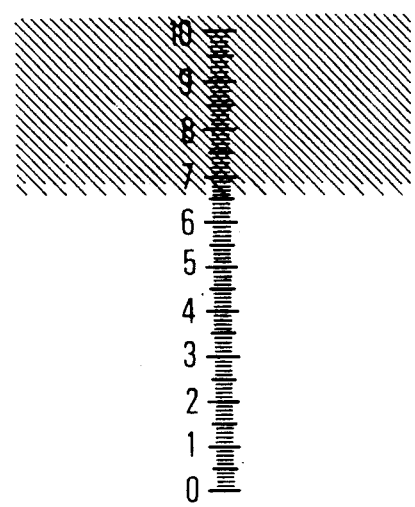
DEGREES BRIX
FIG. 2B (PRIOR ART)
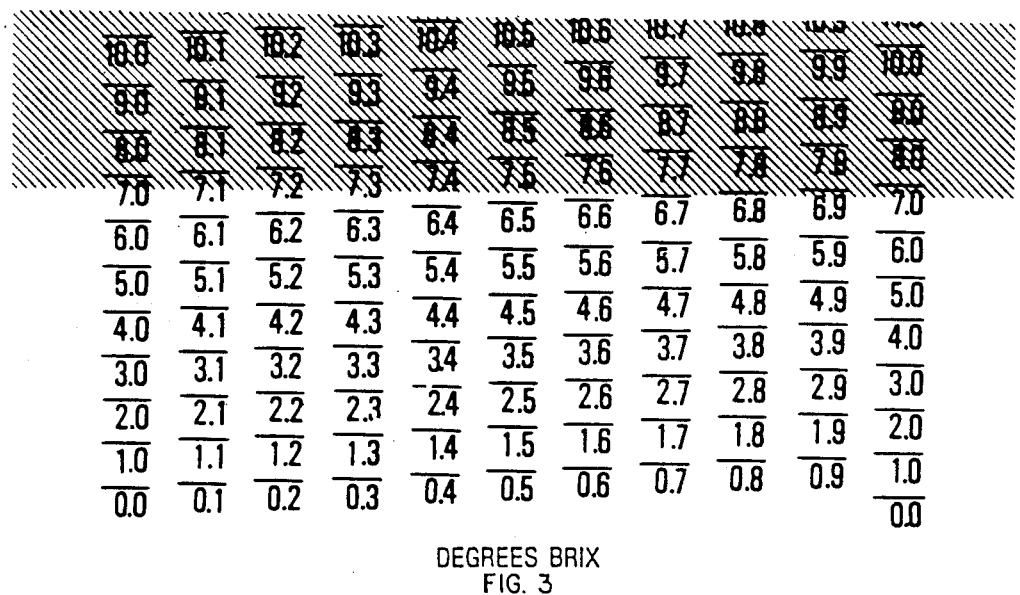
DEGREES BRIX
FIG. 3
DEGREES BRIX
FIG. 4

DEGREES BRIX

FIG. 5

DEGREES BRIX

FIG. 6

REFRACTOMETER READOUT SYSTEM

SUMMARY OF THE INVENTION

This invention is directed to a system of Direct Numerical Readout, allowing conventional hand refractometers to be read with the accuracy and reliability heretofore characteristic of visually read digital bench instruments.

BACKGROUND OF THE INVENTION

Refractometers are commonly used to assess the maturity of fruit before harvest, to control processing in the food and beverage industries, and to check any industrially or clinically useful liquid for deterioration, adulteration, or error in preparation.

Most industrial refractometers are based on the measurement of the Critical Angle of Total Reflection and this invention applies to the most commonly used types which are read visually and do not depend on electronic devices to produce an output automatically.

Since the theory of critical angle refractometers may be found in textbooks on optics as well as in the patent literature (e.g. U.S. Pat. No. 3,267,795), it will be sufficient here to repeat that the measurement is carried out by reading the position of the edge of a dark area which appears in the field of view of the instrument. This edge is often called the refractometer Shadow Line and its exact position in the field of view is a function of the refractive index of the substance being tested. It may be read by either of two methods:

1. Bench Refractometers

In the so-called "Bench" or "Abbe" refractometers the observer looks first through an eyepiece and uses an external manual control to establish coincidence of the Shadow Line with a crosshair or other fixed reference mark positioned in the field of view. He then reads the result of the setting on a separate indicator, which may be calibrated in refractive index units, percent sucrose, freezing point, or any other units of interest.

Bench refractometers have the important advantage that there is no limit to the number of easily readable scale units that may be displayed on a separate indicator. A range from 1.3000 to 1.7000 refractive index units with digital readout of 0.0002 (2000 scale units) is common. Their main drawback for industrial applications is bulk, cost, the time required to first set and then read the instrument, and the difficulty of quantifying the uncertainty of reading caused by an unsharp shadow line which may be due to the nature of the substance being tested or to contamination of the measuring surface.

2. Hand Refractometers

Hand refractometers are compact, portable instruments intended for use in the field, on the factory floor, as well as in the laboratory. Size, weight, cost, sturdiness of construction, and a speedy, reliable readout are important design considerations. In hand refractometers the Shadow Line is imaged directly onto a fixed optical scale which is positioned in the field of view of the instrument, crossing the refractometer Shadow Line at about 90 degrees. The position of the Shadow Line may thus be read directly on that scale.

The hand refractometer system of readout saves time. It also directs the observer's attention immediately to any uncertainty of reading caused by an unsharp Shadow Line. It allows him to read its width directly on the scale and to judge its acceptability.

However, because of optical and mechanical limits to the diameter of the field of view it has not been possible to extend laboratory hand refractometer scales beyond 300 to 500 scale divisions, every tenth division being numbered. For the lower cost industrial instruments the limit is 150 to 250 somewhat larger scale divisions, with every fifth division being numbered. In either case there is no space on hand refractometer scales to put numerals on every or every other scale division. The counting of the un-numbered divisions takes time and is a source of serious errors.

OBJECT OF THE INVENTION The object of this invention is to provide means to read hand refractometer scales with the accuracy and ease heretofore reserved for digital bench refractometers, while retaining the advantages of immediate readout, sturdiness of construction, and low production cost.

Another object of the invention is to provide simple and reliable ways of applying it to hand refractometers of conventional design.

Still another object of the invention is to make its operation self evident to the user and to eliminate the need for directions.

DESCRIPTION OF THE DRAWINGS

The invention is illustrated by way of example in the drawings, where

FIGS. 2a and 2b show a portion of fields of view as seen in a contemporary hand refractometer.

FIG. 3 shows the field of view as seen in hand refractometers equipped according to one form of the invention.

FIGS. 4, 5 and 6 show combined scale patterns which are particularly useful for carrying out the invention.

Turning now to FIG. 1, the substance to be measured 1 is shown between the entrance face of measuring prism 2 and cover plate 3 of the refractometer. Objective 4 images light beams 5 and 6 onto a reticle 7 which carries scale divisions 8. The Shadow Line, which is produced by refraction of a tangential light beam 9 at the interface 12 between substance 1 and measuring prism 2, is imaged at point 10 of reticle scale 8. It is viewed by the observer through eyepiece 11. The location of point 10 on scale 8 is a function of the refractive index of substance 1.

FIGS. 2a and 2b respectively show refractometer scales used heretofore as they would appear to an observer if, for instance, a 6.7% pure sucrose solution (2a) and commercial tomato juice (2b) were measured. Attention is drawn to the lack of sharpness of the shadow line which is characteristic of tomato juice and the resulting uncertainty of reading estimated here at 0.3%. The scales are graduated in percent sucrose, a unit of measurement called degree Brix, which is used commonly in the food industry. They are non-linear. The type of scale shown in FIGS. 2a and 2b will be referred to below as a Conventional Scale.

Figure 1:
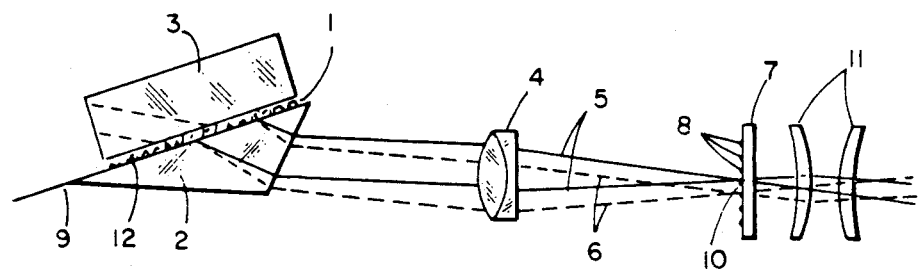
FIG. 1 is a schematic view of a contemporary hand refractometer optical system.

The practical lower limit for the width of Conventional Scale lines as viewed through the eyepiece is about 1 minute of arc ('), and the angular spacing of adjacent scale lines, center to center, should be at least 3' or 4', a minimum spacing that appears unpleasant at times, particularly if the eyepiece is not perfectly focussed by the observer. The numerals should be at 15' or 20' high and their vertical spacing should be about 20' for reasonable ease of reading. Since the minimum vertical pitch of the numerals would thus be about 40', only every tenth division of a Conventional Scale can carry a numeral under these assumptions. The ease of reading can be improved, for instance by shortening every second scale line, lengthening every fifth, and by placing numerals alternately on both sides of the scale, but even then, experience shows that the 6.7% position of the Shadow Line shown in FIG. 2a will be viewed at times as 6.6% or as 6.8%.

THE INVENTION

The problems of scale readability in hand refractometers descried above can be resolved by employing a novel scale pattern, occupying the entire area of the field of view This scale design affords ample space for numbering every scale division. FIG. 3 shows one example of the improved arrangement.

Comparing FIG. 2a with FIG. 3, it is seen that every scale division shown in FIG. 2a also appears in FIG. 3, but that the conventional one-dimensional scale pattern of FIG. 2a has been separated into ten vertical columns or sets of scale lines which have been positioned side by side laterally across the field of view.

Each of these vertical columns is composed of scale divisions representing readings ending with identical numerals: the first column is composed of the whole number scale divisions reading 0.0, 1.0, 2,0, 3.0, etc. The second column comprises the one tenth divisions 0.1, 1.1, 2.1, 3.1, etc., the next the two tenth divisions 0.2, 1.2, 2.2, 3.2 etc., and so on until the tenth column which is made up of the 0.9, 1.9, 2.9, 3.9. etc. scale divisions. An eleventh column which repeats the first has been added to provide a way to check the alignment of the scale with the Shadow Line and for convenience. The reading is taken at the scale line which is positioned nearest to, or just covered by, the Shadow Line. This pattern of columns occupies much more, space laterally than conventional refractometer scales. It will be referred to below as a Direct Numerical Readout Scale.

Using the numbers given above, it is seen that the pattern of FIG. 3 provides a minimum vertical separation of scale lines of 40 minutes of arc. It allows ample space for fifteen or twenty minute numerals to be placed within the bright portion of the field of view, just below or above each scale line, depending on the optical design. This pattern eliminates the unpleasant appearance of narrow spacings and permits half divisions to be estimated more easily.

Several factors must be considered in the design of Direct Numerical Readout Scales: The number of vertical columns is one of them, and in order to determine it, the pattern of FIG. 3 may be thought of as being composed of several sloping segment, which form a continuous scale, rather than of the vertical columns described above. Referring again to FIG. 3, the sloping segments would be the 0.0, 0.1, 0.2, to 1.0 segment at the bottom, then the 1.0, 1.1, 1.2, to 2.0 segment and so on, ending up with the 10.0 to 11.0 segment at the top of the figure.

The vertical spacing of successive sloping segments has to be sufficient to accommodate the numerals and provide adequate vertical separation between them. It is controlled by the number of scale units per sloping segment N, which should be $N = S/W$, where W is the pitch of the smallest scale, divisions, and S is the spacing of successive segments needed for good readability.

In the example given above these dimensions were $W = 4'$ and $S = 40'$, therefore there should be at least ten units in each sloping segment. FIG. 3 shows a pattern where each segment comprises ten 0.1% units, covering a 1.0% span. If the scale units were 0.2% rather than 0.1%, then each sloping segment would cover a 2% span as shown in FIG. 6.

In cases where several scales must be placed side by side within the same field of view, the scale pattern can be narrowed by reducing the number of scale units per segment. The vertical spacing of adjacent segments will then decrease and the scale will appear more crowded, but it will still remain readable with as few as four or five units per segment.

Hand refractometers equipped with the Direct Numerical Readout scales described above have proven easy to read and reliable in practical tests. There have been some instances however, where the improved instruments were used interchangeably or side by side with conventional refractometers, and where observers, who had not been informed of the improved scale, were surprised and did not trust the novel pattern. This contingency can be overcome by combining the Direct Numerical Readout pattern with a Conventional scale as shown in FIGS. 4, 5 and 6. The two scales yield the same reading, so an operator who is familiar only with conventional refractometers, can read the Conventional Scale shown at the left using it as a teaching scale. The operator would see or would be told later that accurate readings can be obtained more easily on the Direct Numerical Readout scale shown at the right using it as a working scale.

Figures 5, 6:
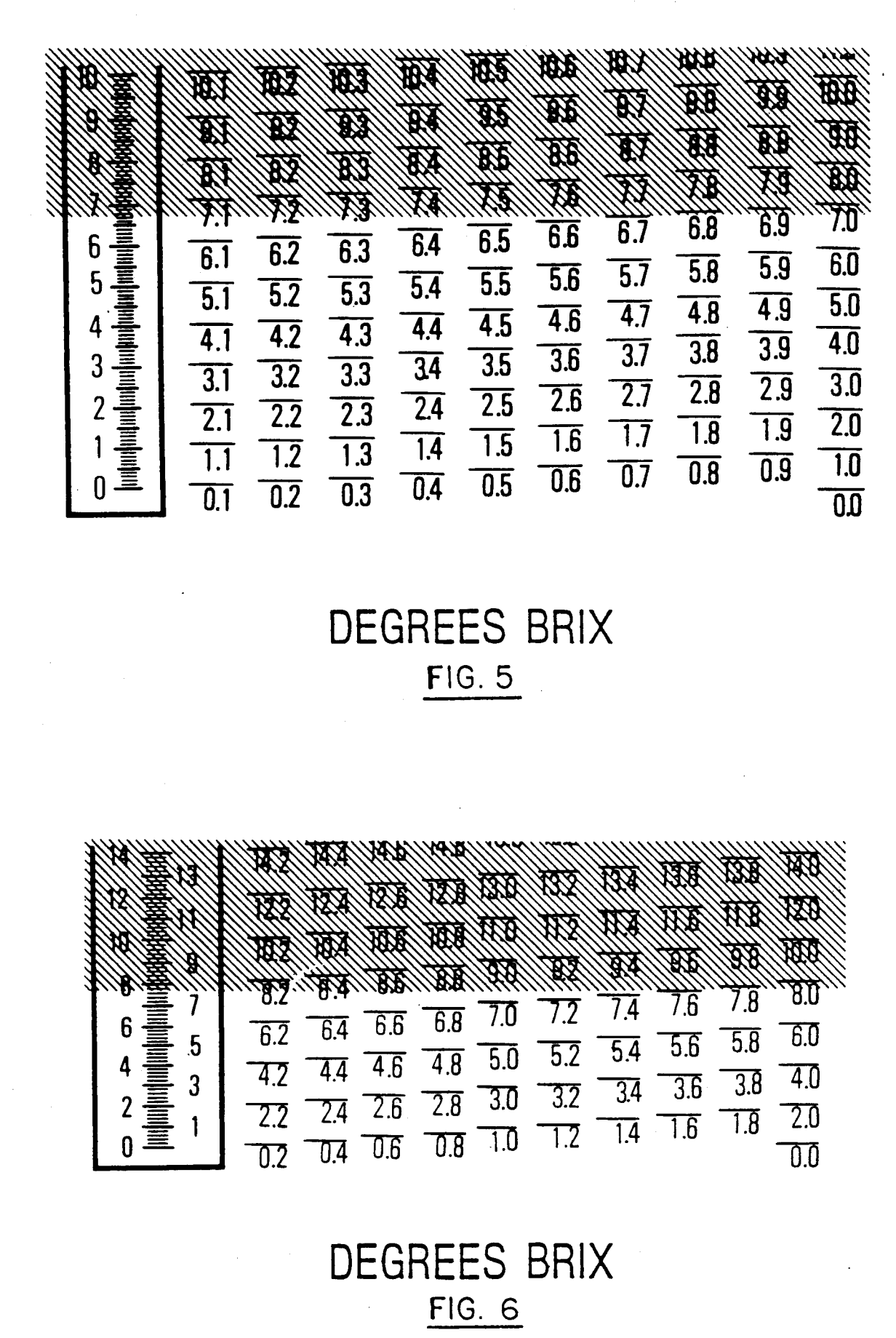

Attention is drawn to the rectangular border which frames the conventional scale in FIGS. 5 and 6. It was found that a graphic separation of the two scale patterns is important because it reduces the uncertainty felt by personnel unfamiliar with measuring instruments when they first see a field of numbers. A solid frame was found to serve the purpose well, but there are many other graphic ways to separate the two patterns, such as a wider spacing, dotted lines, or different styles of numbering.

An important factor peculiar to Direct Numerical Readout scales concerns the method of mounting and adjusting them. The angular position of the conventional one-dimensional refractometer scale with respect to the Shadow Line is set at the factory. It is not adjustable externally because angular changes would affect the reading only according to a cosine relationship and small changes would not, be noticeable. However, the Direct Numerical Readout scales described above are more sensitive to errors in orientation because of their geometry. For instance, a half degree misalignment could cause readings taken at the first and last columns to differ by a scale division and would be noticed at every zero check. Although such changes are unlikely because of the resistance to torsion of the refractometer body, there has to be an external adjustment of the angular setting of the scale pattern for use at assembly and repair. This angular setting must not be affected by subsequent zero adjustments and should not be immediately accessible to the user.

Figure 7:
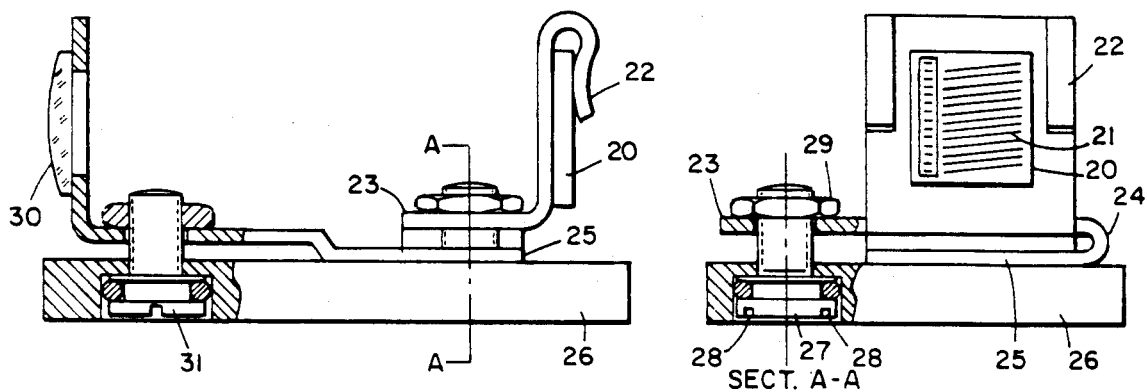
FIGS. 7 and 8 show reticle mounts and objective mounts useful for carrying out the invention.

A practical way of mounting the reticle so as to satisfy the foregoing requirements is shown in FIG. 7. The reticle 20 carries the Direct Numerical Readout scale 21 and is attached by resilient members 22 and/or cement to the upper leg 23 of the "U" shaped reticle carrier 24. The lower leg 25 of the "U" is fixed, being fastened to the refractometer body 26. The orientation of the upper leg 23 controls the alignment of scale and Shadow Line. It is set with respect to the refractometer body 26 by a gasketed screw 27 which engages nut 29 mounted on upper leg 23. A special tool engaging holes 28 of the screw head is required for adjustment to prevent the user from changing the setting without prior consideration.

The reading of the scale is adjusted by moving the objective lens 30 vertically, using the gasketed screw 31. Since movement of a lens does not affect the angular orientation of the image formed by it, this adjustment does not disturb the alignment between the scale pattern and Shadow Line. It should be the last adjustment made.

Figure 8:
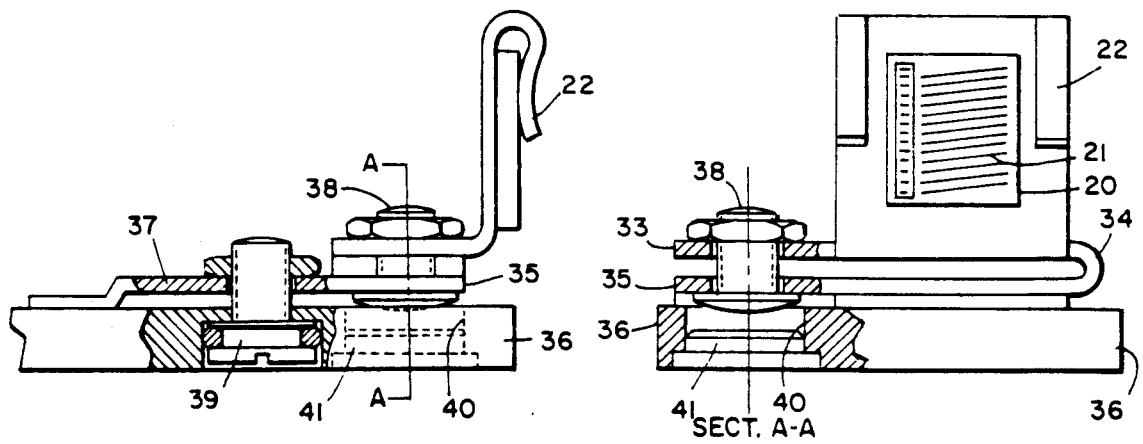

An alternate system of reticle adjustment is illustrated in FIG. 8. The reticle carrier 34 is the same as carrier 24 of FIG. 4, but the lower leg 35 of the "U" is connected to the refractometer body 36 through a resilient member 37 rather than directly. The orientation of the upper member 33 of the "U" is set at the factory by adjusting screw 38, which acts between legs 33 and 35, floating with respect to the refractometer body 36. It is reached through an access hole 40 and protected from immediate access by a rubber plug or cover screw 41. The zero setting of the instrument is controlled by a gasketed screw 39 which raises or lowers the reticle assembly as required.

Having described my invention, what I claim is:

1. In a refractometer of the critical angle of total reflection type
   a scale for reading the concentration of a substance to be measured, an optical system including an objective to form an image on a reticle carrying said scale, said image including a shadow line moving across said scale in a direction of measurement in response to changes of said concentration to be measured, and
   said scale being composed of scale segments, and
   said scale segments being composed of successive scale divisions oriented parallel to said shadow line and positioned stepwise end-by-end, and
   said scale segments sloping laterally to said direction of measurement, and forming angles of orientation with respect to said show line.
   said sloping scale segments being positioned with respect to each other to form a continuously reading scale, and
   identifying numerals being positioned adjacent to at least one half of the said successive scale divisions to form discrete reading units providing a direct numerical readout of said concentration of said substance to be measured.

2. A scale according to claim 1,
   each of said sloping scale segments comprising a beginning scale division and an ending scale division, and each of said beginning scale divisions repeating the reading of said ending scale division of the preceding said sloping scale segment.

3. In a refractometer according to claim 1, a housing and an inner assembly for holding said reticle and said objective lens, and
   first adjustment means operative to adjust said angles of orientation of said sloping scale segments with respect to said shadow line, and
   second adjustment means operative to adjust the position of said shadow line on said scale divisions without altering said angles of orientation, and
   said first adjustment means being less accessible for adjustment than said second adjustment means.

4. A refractometer according to claim 3,
   said first adjustment means acting between said reticle and said housing, and said second adjustment means acting between said objective lens and said housing.

5. A refractometer according to claim 3,
   said first adjustment means acting between said reticle and said inner assembly, and said second adjustment means acting between said inner assembly and said housing.

6. A refractometer of the critical angle of total reflection type, comprising an optical system having a field of view, and imaging a shadow line on a reticle positioned within said field of view, and
   said reticle comprising a teaching scale and a working scale, both said scales being visible at the same time, and
   both said scales producing similar readings, and
   said teaching scale being a conventional scale, and said working scale being a scale according to claim 1.

7. A refractometer according to claim 6
   said reticle comprising graphic means operative to visually separate said teaching and said working scales within said field of view.

* * * * *